United States Patent [19]

Hale

[11] Patent Number: 5,674,243

[45] Date of Patent: Oct. 7, 1997

[54] OBSTETRICAL FORCEPS

[76] Inventor: Theodore Mark Hale, 39 Celano La., West Islip, N.Y. 11795

[21] Appl. No.: 510,958

[22] Filed: Aug. 3, 1995

[51] Int. Cl.⁶ .................................................. A61B 17/28
[52] U.S. Cl. ........................... 606/205; 606/119; 606/122
[58] Field of Search ..................... 606/119, 121, 606/122, 124, 210, 205, 207, 157, 133, 131

[56] References Cited

U.S. PATENT DOCUMENTS

| 2,637,320 | 5/1953 | Greenberg | 606/122 |
|---|---|---|---|
| 3,384,088 | 5/1968 | Miseo | 128/323 |
| 3,550,595 | 12/1970 | Laufe | 606/122 |
| 3,592,198 | 7/1971 | Evans | 128/352 |
| 3,779,248 | 12/1973 | Karman | 128/321 |
| 3,789,849 | 2/1974 | Laufe et al. | 606/122 |
| 4,165,746 | 8/1979 | Burgin | 128/321 |
| 5,002,561 | 3/1991 | Fisher | 606/205 |
| 5,019,091 | 5/1991 | Porat et al. | 606/205 |

OTHER PUBLICATIONS

Obstetrics and Gynecology 5th Ed., D. Danforth et al. eds., "Dystocia Due to Abnormal Fetopelvic Relations," pp. 691–698 (1986).

ACOG Technical Bulletin, No. 196, Operative Vaginal Delivery (Aug. 1994).

*Primary Examiner*—Michael Buiz
*Assistant Examiner*—Kevin Truong
*Attorney, Agent, or Firm*—Collard & Roe, P.C.

[57] ABSTRACT

Obstetrical forceps fabricated from a flexible material, preferably a low residue polyurethane elastomer, to facilitate safe delivery of a fetus.

5 Claims, 5 Drawing Sheets

OBSTETRICAL FORCEPS

FIELD OF THE INVENTION

The present invention relates to improved surgical instruments and more particularly to improved obstetrical forceps.

BACKGROUND OF THE INVENTION

Obstetrical forceps have long been in use in the medical profession and known in the medical literature. Obstetrical forceps are utilized to aid in fetal delivery by allowing the physician to adjust the position of the unborn child's head during delivery. Obstetrical forceps also allow the physician to apply traction to the unborn child's head to assist in the birthing process. While nearly 20 types of obstetrical forceps are currently in use, most are modifications of the so-called classic forceps with the standard cephalic and pelvic curves and typically made of stainless steel. Such conventional forceps present serious risk of injury to both the mother and particularly to the unborn child. All forceps constructed of stainless steel or similarly rigid material are capable of applying forces to the unborn child's head which the head cannot tolerate. Such applied force can be compressive when the forceps are closed upon the head, or rotational or tractional when the engaged forceps are rotated or pulled by the physician. It is entirely dependent upon the operating physician to limit the level of applied force to that which can be tolerated by the fetal skull. Due to the similarity in construction of presently available obstetrical forceps, achieving successful results has depended more on the skill and judgment of the operator than on the selection of any particular forceps. While data regarding forces generated by obstetrical forceps has been accumulated, this represents only a small fraction of the information relating to how such forces can affect the fetal skull complicating the physician's efforts to utilize obstetrical forceps safely. Neither the hardness of the fetal head nor the tensile properties of the intact fetal skull are well known. Similarly, the tear resistance of the membranes forming the structure of the brain or the flexural modules (bending stiffness) of the skull during delivery are not well known or characterized.

One method of overcoming this problem is described in U.S. Pat. No. 2,637,320('320 patent) to Greenberg. The '320 patent provides obstetrical forceps wherein the blades of known forceps are coated with a pliable elastic material. Air is introduced between the steel of the blades and the pliable elastic coating thereby inflating the blades and providing the operator with adjustable and cushioned forceps. Alternatively, an inflatable sheath can be removably fixed over the blades. The sheath can subsequently be inflated to provide similar adjustability and cushion. However, this device is complicated and is limited by the durability of the inflation sleeves, the uniformity of pressure that can be applied and the difficulty in controlling the extent of inflation of the sleeves.

SUMMARY OF THE INVENTION

It is an object of the present invention to provide obstetrical forceps that are lighter than conventional metal forceps.

It is another object of the present invention to provide obstetrical forceps that are more flexible than conventional metal forceps.

It is a further object of the present invention to provide obstetrical forceps fabricated from a flexible material, preferably a modern low residue polyurethane elastomer to facilitate safe delivery of a fetus.

It is yet a further object of the present invention to provide obstetrical forceps made of polyurethane, wherein the blades of such forceps are made entirely of polyurethane.

The forceps of the present invention are more similar to the fetal skull in hardness and elasticity than conventional forceps, and thereby reduce the risk of injury to a fetus when the use of obstetrical forceps is indicated during delivery. By providing obstetrical forceps manufactured entirely from a flexible material, preferably polyurethane, the present invention increases the safety of using obstetrical forceps during childbirth. The elasticity of polyurethane elastomer allows for more even distribution of the forces applied to the fetal skull than is encountered when using conventional steel forceps. When using conventional steel forceps in circumstances where the curvature of the obstetrical blade does not precisely match that of the fetal skull, there is a risk of applying too much pressure to a limited contact area. When an operating surgeon applies pressure to the obstetrical forceps of the present invention, however, the elasticity of the polyurethane allows the preformed blades to partially deform to better engage the fetal skull. This desirable deformation of the obstetrical forcep blades reduces the probability of exerting excessive pressure from building up in a limited contact area and being transmitted to the fetal brain which in some cases results in hemorrhaging within the fetal brain.

The obstetrical forceps of the present invention may be made by injection molding techniques which are well known in the art. Injection molded polyurethane is a preferred method and material of construction because low residue polyurethanes exhibit both toughness and resilience in addition to bacterial resistance which makes it preferred material for the obstetrical forceps of the present invention. Additionally, the non-porous surface characteristics of polyurethane makes it well suited for gas sterilization. Furthermore, as the obstetrical forceps of the present invention are injection molded, production costs will be substantially less than that of conventional stainless steel forceps currently in use. By reducing the cost of manufacture, the obstetrical forceps of the present invention will be readily available in third world countries where practitioners are unable to afford the more expensive conventional stainless steel forceps. It is also envisioned that with reduced manufacturing costs, the price of the obstetrical forceps of the present invention may allow the forceps to become a single use throw away instrument, thereby eliminating any threat of disease transferral and eliminating the time and expense encountered with sterilization. An additional benefit of using polyurethane in the construction of the present invention is enhanced patient comfort. Due to the low thermal conductivity of polyurethane, the chilling effect experienced with conventional stainless steel obstetrical forceps is eliminated.

The obstetrical forceps of the present invention is comprised of two members. Each member of the forceps has a handle area, a pivot/hinge area and a blade area. The two members or halves are disengageably and rotatably joined at the pivot/hinge area to form a pair of usable forceps.

The handle area of the forcep of the present invention is shorter than conventional obstetrical forceps, thereby allowing for one handed operation of the forceps. By shortening the handle length, the moment arm is shortened thereby reducing and limiting the force which my be applied at the contact point of the blade areas. Additionally, in a preferred embodiment, the handle area of the present invention is preferably smooth, thereby limiting the tractional force which may be applied by the physician.

The pivot/hinge area is designed to allow each half to interjoin with the other and may be of any well known construction. In a preferred embodiment, the hinge area on each half is substantially thicker than that found on conventional forceps. This thickened area is a modification which allows the forceps to be made of polyurethane while retaining the necessary rigidity and durability to function properly. The hinge area is two tiered, with a recessed area for receiving the pivot of the opposing half. The orientation of the recessed hinge area and the pivot on each half is complimentary to each other allowing the two halves to rotate about the pivot of the other. The blade area is of a new closed blade design and is thicker than blades of conventional forceps to allow for the use of polyurethane as the only material in the blades.

An alternative and preferred construction of the obstetrical forceps of the present invention is also presented. To assure proper rigidity of the forceps of the present invention, a stiffening core my be incorporated in the construction of the forceps. The stiffening core my be made of any substantially rigid material. The preferred material for the stiffening core is stainless steel, and most preferred is 303 stainless steel. The stiffening core is encapsulated within the polyurethane body of the forceps within the handle area, the pivot/hinge area and the shank region of the blade area of the forceps. The stiffening core does not extend substantially into the blade area thereby allowing the blades of the forceps to maintain their elasticity and flexibility. By providing a stiffening core within the handle and pivot/hinge area of the forceps, the necessary strength and rigidity is assured at the hinge area which is narrow and under substantial load. The stiffening core also provides substantial rigidity to the handles and provides the practitioner definite and positive control over the forceps.

The present invention will be further understood and appreciated from the following detailed description and claims taken in conjunction with the drawings.

PIG. 3 is a side perspective view of the forceps of the present invention wherein the two halves are interjoined in a closed position.

Figure 4:
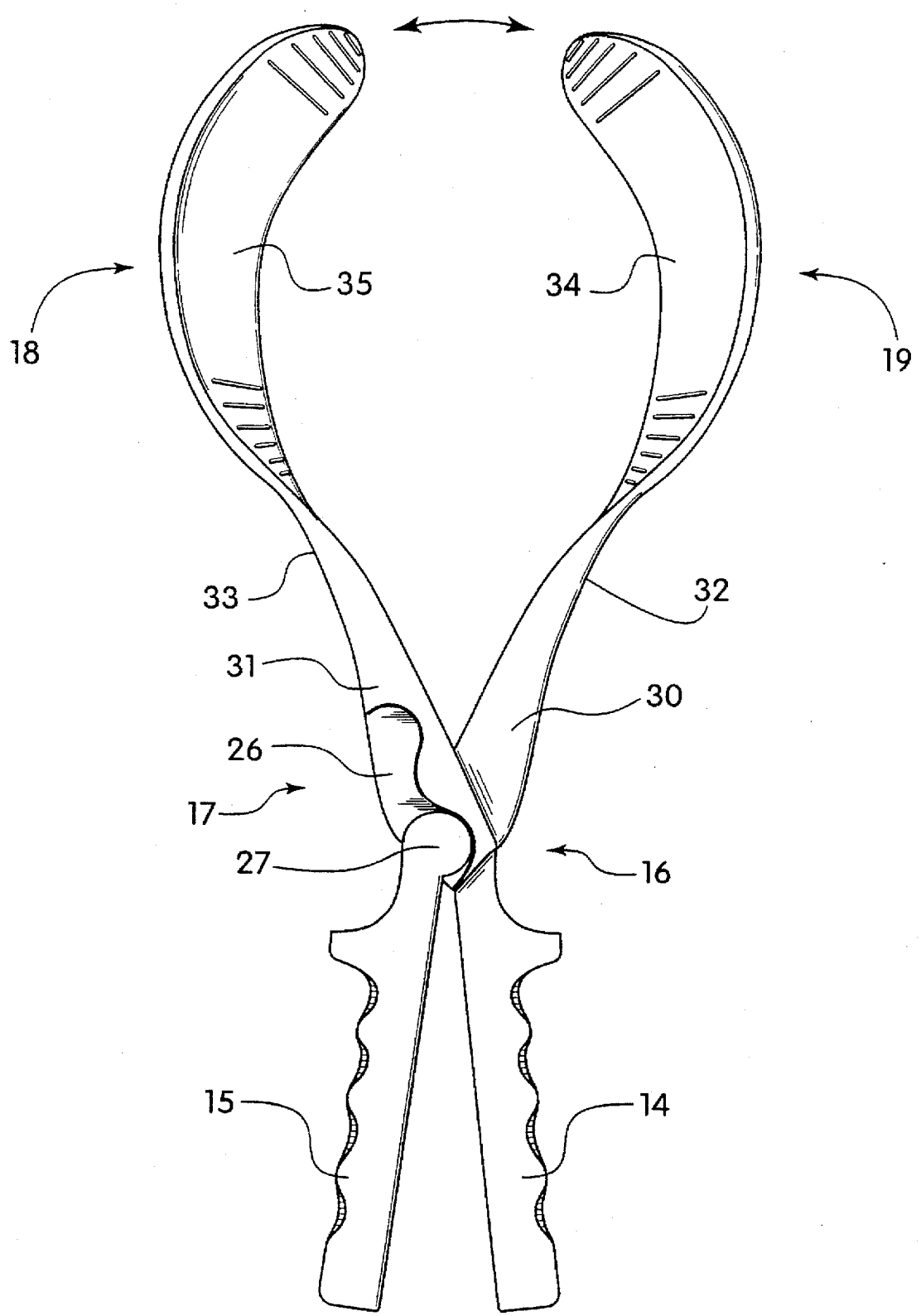

FIG. 4 is a perspective view of the forceps of the present invention wherein the two halves are interjoined in an open position.

Figures 5, 6:
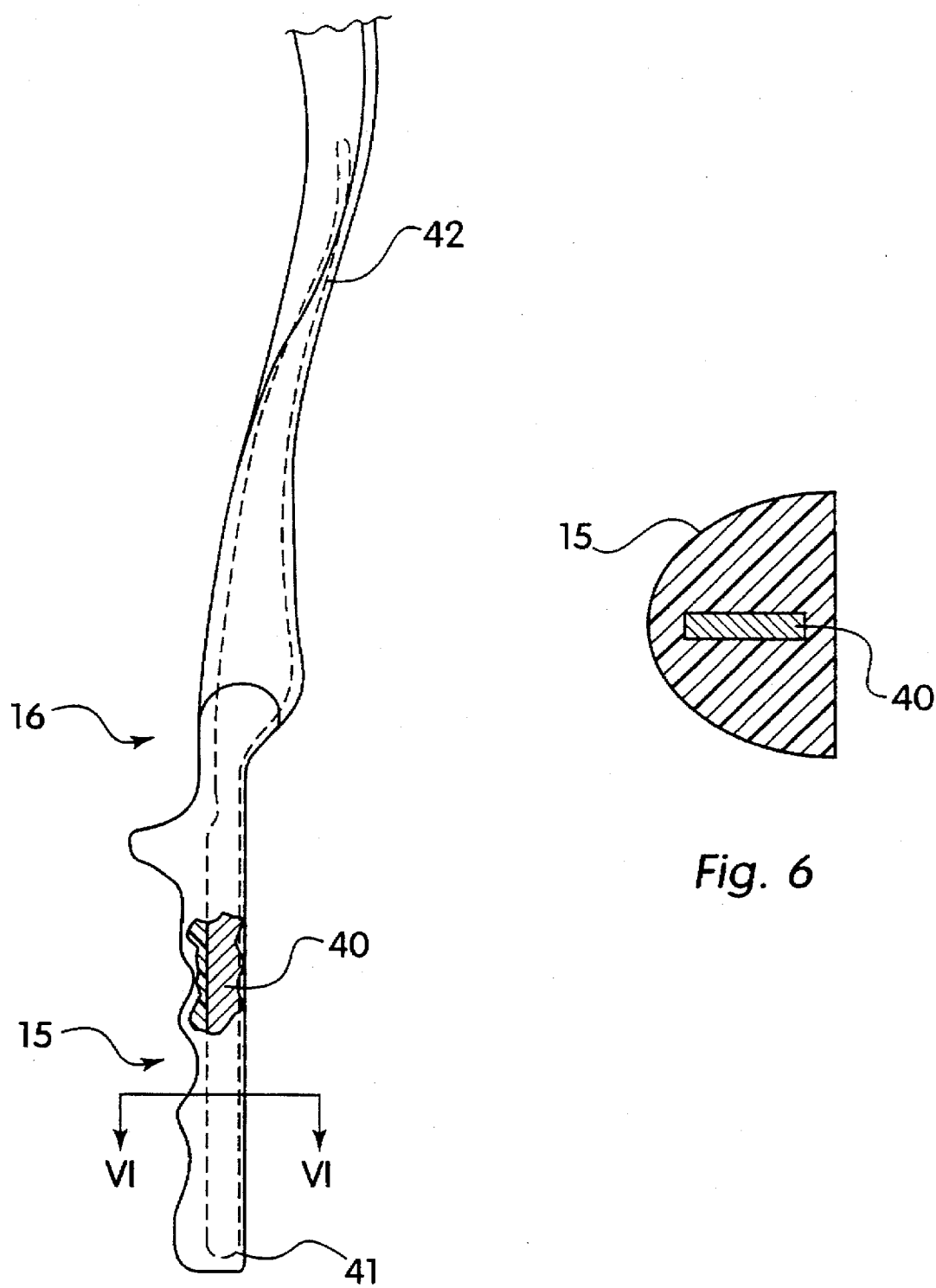

FIG. 5 is a partial view of one half member of the forceps with a partial cut-a-way view showing the internal stiffening core.

FIG. 6 is a cross-sectional view of the handle of the present invention showing the stiffening core.

DETAILED DESCRIPTION OF THE INVENTION

Figure 1:
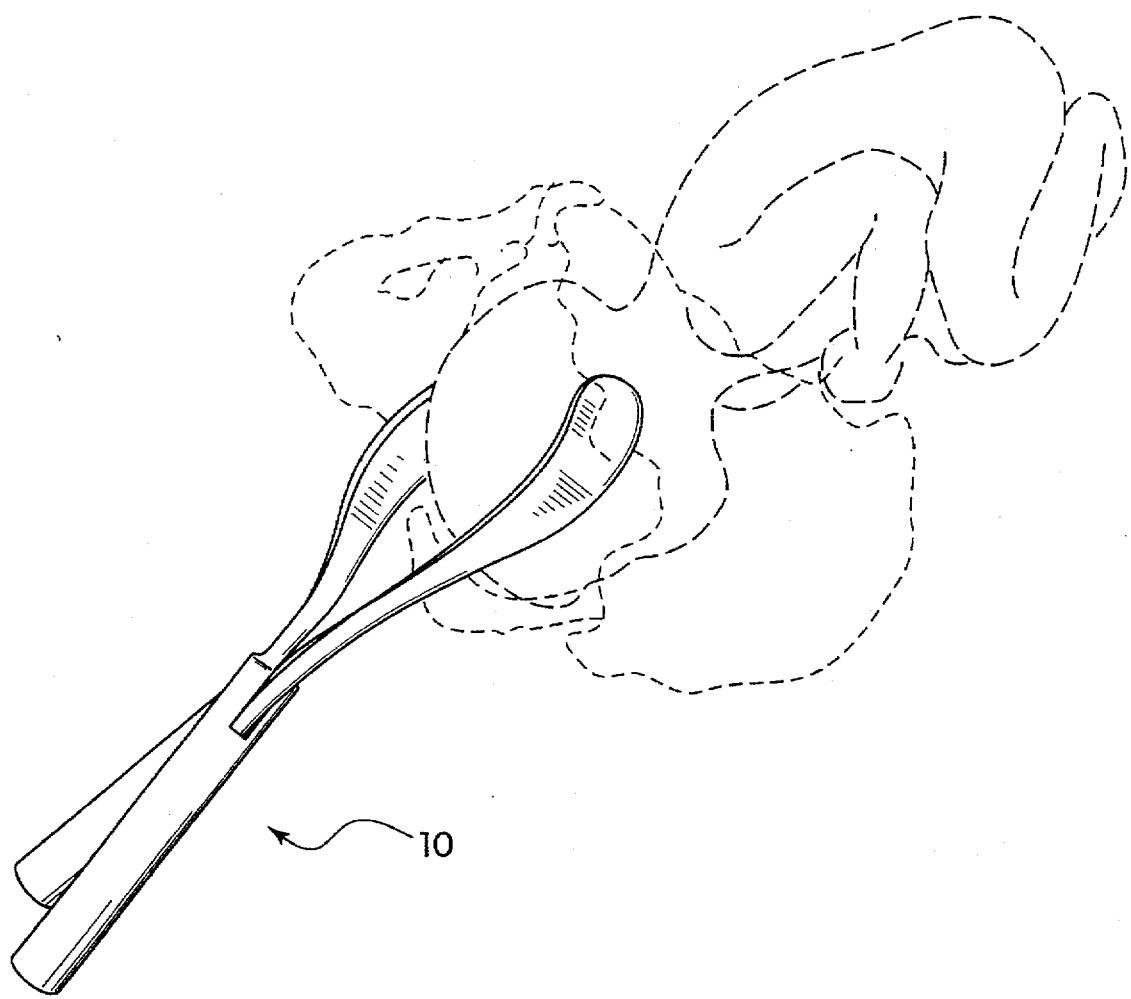
FIG. 1 shows the use of one embodiment of the obstetrical forceps of the present invention.
Figure 2:
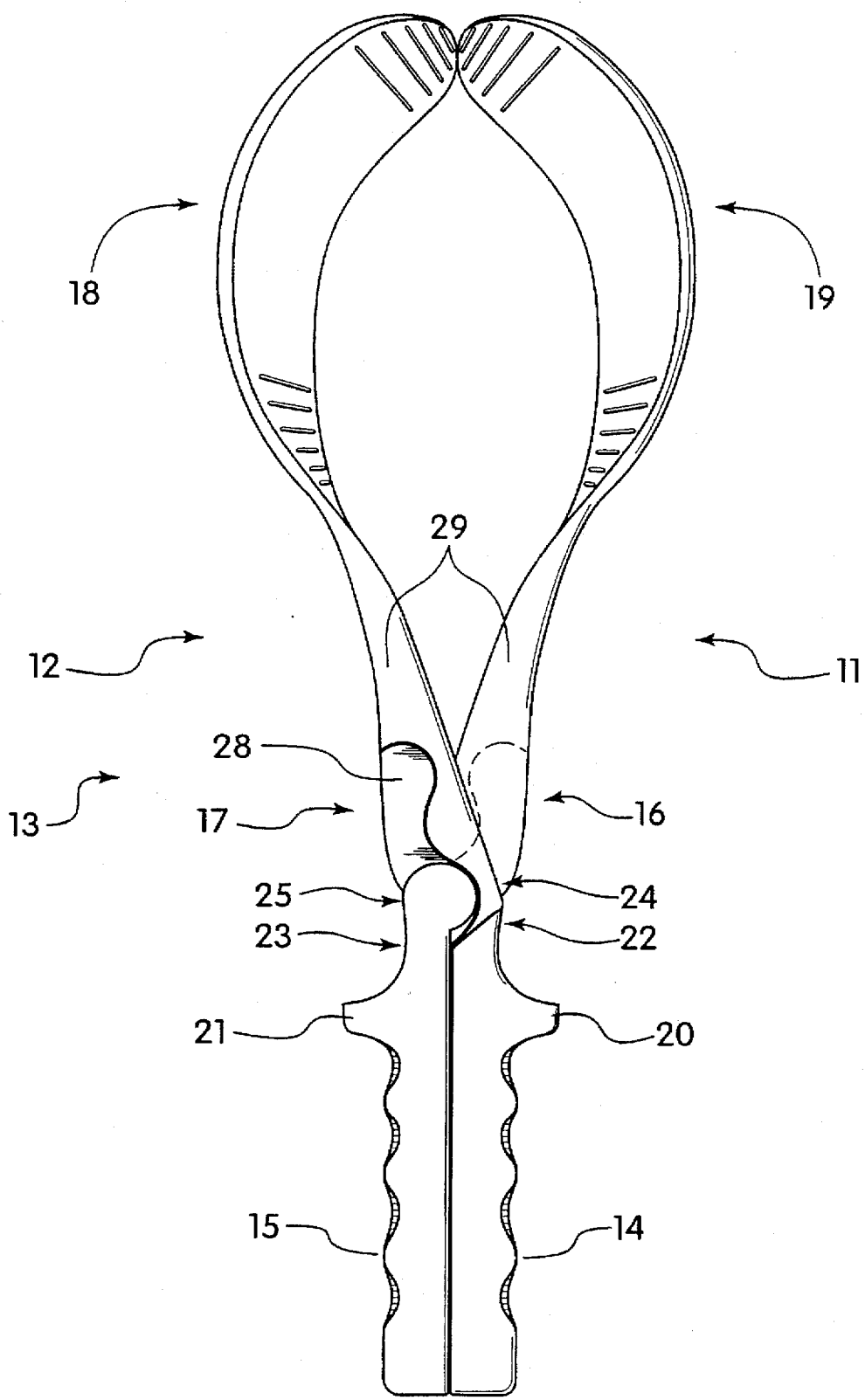
FIG. 2 is a perspective view of the forceps of the present invention wherein the two halves are interjoined in a closed position.

Referring now to the drawings, and particularly to FIGS. 1–5, there is shown an obstetrical forceps 10 embodying one form of the present invention. FIG. 1 shows the obstetrical forceps of the present invention engaging a fetal head for assisting delivery. FIG. 2 shows forceps 10 which includes a pair of elongated members 11 and 12, pivotally connected to each other at an intermediate position, the interlocking joint 13, along the length of the members to form what is commonly known as a cross-type forceps.

As shown in FIG. 2, each member 11 and 12 comprises handle portions 14 and 15, pivot/hinge portions 16 and 17 and blade portions 18 and 19. The handle portion is located at the proximal end of each member. Handle portion 14 is shaped to compliment handle portion 15 thereby allowing the handle portions to fit together to form a complete handle for gripping by an obstetrician. Handle portions 14 and 15 are provided with the usual contoured finger gripping surface for facilitating gripping by a hand. Alternatively, the handles may be smooth to limit the tractional grip provided to the obstetrician. The handle portions 14 and 15 are shorter than handles found on conventional obstetrical forceps. Preferably, the handle portion is long enough for use by one hand and fitting substantially entirely within one hand. This shortened handle length acts to limit the force that may be delivered to the obstetrical forceps blades 18, 19 by limiting the length of the moment arm. Each handle portion 14 and 15 are also provided with at least one lateral finger grip 20, 21 for providing an additional purchase for the obstetrician's fingers while utilizing the forceps. The distal region of the handle portions 22 and 23 adjoin the proximal portions of the pivot/hinge areas 24 and 25.

The pivotable connection between the members 11 and 12 comprises pivot hinge areas 16 and 17 of any well known construction to permit free pivotable movement between the members while allowing free separation of the members without the necessity of unbolting or unscrewing parts. In a preferred embodiment of the present invention the pivotable connection between the members 11 and 12 is formed at the interlocking joint 13 as shown in FIG. 2. As shown in FIG. 4 the pivot/hinge areas 16, 17 of each member comprises a hinge 26 and a pivot 27. The hinge 26 is two tiered with a recessed area for receiving the pivot 27 of the opposing member. The orientation of the recessed region of the hinge 26 and the pivot 27 on each member is complimentary to the recessed region of hinge 26 and pivot 27 of the other member allowing the two members to interjoin and rotate about the axis of the other member's pivot.

Figure 3:
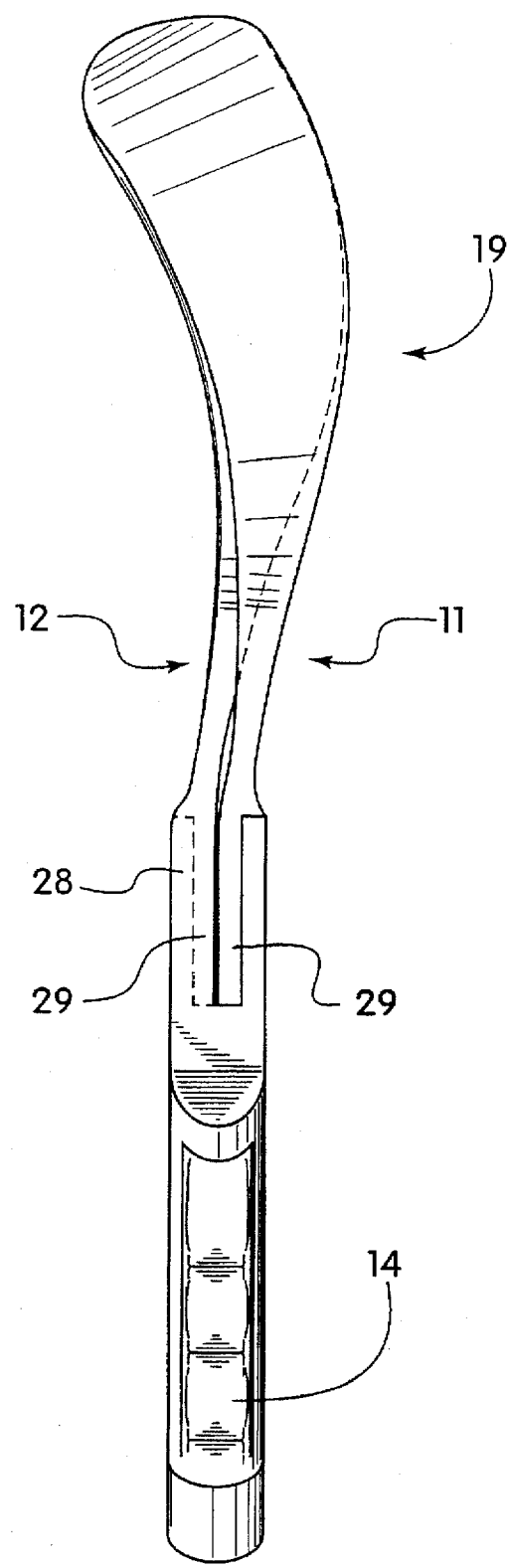

As shown in FIGS. 2 and 3, the two tiered structure 28 of the hinge area provides for a thickened area 29 in the hinge area 26 which is substantially thicker than that found on conventional forceps. This thickened area 29 allows the forceps to be made of polyurethane and still function properly without being permanently and substantially deformed during use.

Blade portions 18, 19 comprise straight shanks 32, 33 and smoothly curved blades 34, 35 fixed to shanks 32, 33. As shown in FIG. 4 the distal proportion of the pivot/hinge areas 30 and 31 are adjacent to the proximal region of straight shanks 32 and 33. The blades 34, 35 are smoothly curved for engaging a fetal head in the manner shown in FIG. 1. When members 11 and 12 are interlocked as shown in FIGS. 2 and 4, manipulation of the handle regions 14 and 15 allow the blade regions to move relative to one another thereby allowing the blade the areas to grasp fetal skull during delivery.

The blades 18 and 19 are constructed entirely of polyurethane and as shown in FIGS. 2, 3 and 4 are of closed blade design. The blades are of a thickness to allow polyurethane, as a sole component, to provide rigidity sufficient for the blades to function properly while retaining the desired properties of elasticity and flexibility.

In a particularly preferred embodiment of the present invention, as shown in FIGS. 5 and 6, each member 11, 12 of the obstetrical forceps contains a stiffening core 40 extending from the proximal region of the handle area 41 through pivot/hinge areas 16, 17 and into the proximal area of the shank region 42 of the blade 18. FIG. 5 is a cross-sectional partial cut-a-way view showing the stiffening core 40 extending along the axis of the member 12. FIG. 6 is a cross-sectional view of the handle region 15 as shown in FIG. 5 showing the stiffening core 40 within the body of the member 15. The stiffening core 40 may be made of any sufficiently stiff material, preferably stainless steel, and more preferably 303 stainless steel. During the manufacture of the obstetrical forceps members 11, 12, the stiffening core 40 will be encapsulated by the polyurethane of the obstetrical forceps. The stiffening core 40 provides rigidity and stability to the handle 15 and pivot/hinge areas 16, 17 of the members 11 and 12. This provides sufficient rigidity and stiffness to the handle, pivot/hinge area and proximal region of the shank portion 42 of the blade 18, 19 without having to make these regions excessively thick to compensate for the natural elasticity and flexibility of the polyurethane. This composite construct also allows the blade areas 18, 19 to be constructed entirely of polyurethane as the stiffening core 40 does not extend beyond the proximal region of the shank portion 42 of the blade 18 as shown in FIG. 5. Thus allowing the blade region to retain the elasticity and flexibility of the polyurethane. When a compressive of force is applied to blade portions 18, 19 as when a fetus is engaged by the complete forceps 10 and given a compressive and traction force, the elasticity and flexibility of blade portions 18, 19 will allow blade portions 18, 19 to slightly deform rather than damage the fetal skull as is possible with conventional steel forceps.

What is claimed is:

1. An improved obstetrical forceps apparatus of the type in which a pair of elongated members are disengageably and pivotally connected to each other at an intermediate position along the length of each member, and in which each member is grippable at a proximal end and smoothly curved for engaging a fetal head at a distal end, wherein the improvement comprises elongated members formed of polyurethane that are flexible and resiliently deformable to limit compressive force applied to the fetal head during use.

2. The apparatus of claim 1 wherein the crosssectional area of the intermediate portion is of an effective size to retain the resilience of each member.

3. An improved obstetrical forceps apparatus of the type in which a pair of elongated members are disengageably and pivotally connected to each other at an intermediate position along the length of each member, and in which each member is grippable at a proximal end and smoothly curved for engaging a fetal head at a distal end, wherein the improvement comprises members formed of polyurethane and a stiffening core extending through the proximal end of each member, but not through the distal end of each member such that the proximal ends are reinforced and the distal ends are flexible and resiliently deformable to limit compressive force applied to the fetal head during use.

4. The apparatus of claim 3 wherein the stiffening core is formed of stainless steel.

5. The apparatus of claim 3 wherein the cross-sectional area of the intermediate portion is of an effective size to retain the resilience of each member.

* * * * *